United States Patent
Mogi et al.

[11] Patent Number: 5,902,826
[45] Date of Patent: May 11, 1999

[54] PLATINUM (IV) COMPLEX AND PHARMACEUTICAL COMPOSITION COMPRISING THE SAME

[75] Inventors: Kinichi Mogi; Hidehiko Koya; Mari Ohtsuka; Hiroyuki Mizuno; Susumu Sato, all of Chiba, Japan

[73] Assignee: SS Pharmaceutical Co., Ltd., Tokyo, Japan, JPX

[21] Appl. No.: 08/997,061

[22] Filed: Dec. 23, 1997

[30] Foreign Application Priority Data

Mar. 14, 1997 [JP] Japan .................................. 9-060645

[51] Int. Cl.$^6$ .............................. A61K 31/28; C07F 15/00
[52] U.S. Cl. ................................. 514/492; 556/137
[58] Field of Search .............................. 556/137; 514/492

[56] References Cited

U.S. PATENT DOCUMENTS

| | | | |
|---|---|---|---|
| 4,658,048 | 4/1987 | Totani et al. | 556/137 |
| 5,648,384 | 7/1997 | Kidani et al. | 514/492 |

*Primary Examiner*—Porfirio Nazario-Gonzalez
*Attorney, Agent, or Firm*—Morgan, Lewis & Bockius LLP

[57] ABSTRACT

A diamine-platinum (IV) complex represented by the following formula (1):

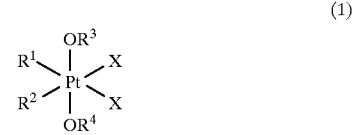

wherein $R^1$ and $R^2$ together represent $R^5O$—$CH(CH_2NH_2)_2$ ($R^5$ represents hydrogen, acetyl, trifluoroacetyl, benzoyl, cycloalkylcarbonyl or methanesulfonyl) or a $C_{5-8}$ 1,2-cycloalkanediamine; $R^3$ and $R^4$ each represents hydrogen or $R^6CO$— ($R^6$ represents alkyl, halogenoalkyl, cycloalkyl, aryl or aralkyl); and two X's together represent a malonic acid residue or glycolic acid residue which may have a substituent capable of coordinating to the platinum in formula (1) by an O,O-coordination or an N-acylamino acid residue coordinating to the platinum in formula (1) by an O,N-coordination; and a pharmaceutical composition comprising as an active ingredient the above-described diamine-platinum (IV) complex.

21 Claims, No Drawings

PLATINUM (IV) COMPLEX AND PHARMACEUTICAL COMPOSITION COMPRISING THE SAME

BACKGROUND OF THE INVENTION

1. Field of the Invention

This invention relates to a platinum (IV) complex having excellent therapeutic effects on malignant tumors and to a pharmaceutical composition comprising the platinum (IV) complex.

2. Discussion of the Background

In recent years, malignant tumors became the top of the cause of death, and various anti-malignant tumor drugs have been developed to treat them. As a platinum complex among these drugs, a cisplatin has already been used. However, the cisplatin sometimes causes serious nephropathy as a side effect, so that its use must often be limited. In addition, since the cisplatin is slightly soluble in water and organic solvents, the route of administration is also limited. In consequence, a carboplatin (*Saishin Igaku*, 41(3):509 (1986)) has been developed and marketed as a derivative of the cisplatin having a reduced renal toxicity and an increased solubility in water. Also, in recent years, in addition to divalent platinum complexes including the cisplatin and the carboplatin as representative examples, tetravalent platinum complexes, typically an iproplatin (a compound disclosed in JP-A-57-77694; the term "JP-A" as used herein means an "unexamined published Japanese patent application"), have been developed. Their antitumor effects have been shown, for example, in JP-A-61-33192, JP-A-61-7283, JP-A-62-207283, JP-A-1-294684, JP-A-2-4797, JP-A-2-96523, JP-A-8-20594, JP-A-8-27174 and JP-A-8-259581. These tetravalent platinum complexes have characteristics in that they have excellent water solubility and low renal toxicity. Some of them have a high lipophilicity and can be orally administered. However, their antitumor effects are not always satisfactory.

SUMMARY OF THE INVENTION

An object of the present invention is to provide a pharmaceutical composition which has superior antitumor effects and can be orally administered.

This and other objects of the present invention have been provided by a diamine-platinum (IV) complex represented by the following formula (1):

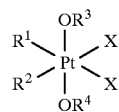

wherein $R^1$ and $R^2$ together represent the following group (A):

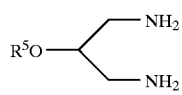

in which $R^5$ represents a hydrogen atom, an acetyl group, a trifluoroacetyl group, a benzoyl group, a cycloalkylcarbonyl group or a methanesulfonyl group, or a 1,2-cycloalkanediamine having 5 to 8 carbon atoms which can represent all stereochemical structures, cis (R,S), trans (1S,2S) and trans (1R,2R);

$R^3$ and $R^4$ are the same or different and each represents a hydrogen atom or a group $R^6CO—$ in which $R^6$ represents a straight- or branched-chain alkyl group, an alkyl group having a halogen atom, a cycloalkyl group, an aryl group or an aralkyl group; and two X's together represent a malonic acid residue or glycolic acid residue which may have a substituent capable of coordinating to the platinum in formula (1) by an O,O-coordination or an N-acylamino acid residue coordinating to the platinum in formula (1) by an O,N-coordination, or a salt thereof.

Furthermore, this and other objects of the present invention have been accomplished by a pharmaceutical composition comprising as an active ingredient the above-described diamine-platinum (IV) complex or a pharmaceutically acceptable salt thereof, optionally together with a pharmaceutically acceptable carrier or diluent.

Moreover, this and other objects of the present invention have been accomplished by a method for preventing or treating a tumor comprising as an active ingredient administering to human or animal in need of such prevention or treatment an effective amount of the above-described diamine-platinum (IV) complex or a pharmaceutically acceptable salt thereof, optionally together with a pharmaceutically acceptable carrier or diluent.

Also, this and other objects of the present invention have been accomplished by use of the above-described diamine-platinum (IV) complex or a pharmaceutically acceptable salt thereof for preparing a pharmaceutical composition.

DETAILED DESCRIPTION OF THE INVENTION

The inventors of the present invention have conducted intensive studies and found as a result of the efforts that a novel platinum (IV) complex represented by formula (1) can resolve the above-described problems and can be used as a drug which is effective for the treatment of malignant tumors and the like, thus resulting in the accomplishment of the present invention.

The diamine platinum (IV) complex represented by formula (1) is roughly divided into the following types (1A) and (1B) depending on the diamines represented by $R^1$ and $R^2$.

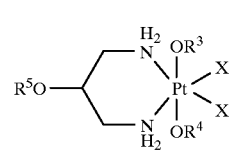

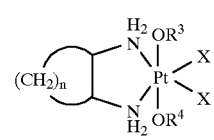

(In the formulae, n is an integer of 3 to 6; and $R^3$, $R^4$, $R^5$ and X have the same meanings as defined above.)

In formulae (1) and (1A) and group A, the cycloalkylcarbonyl group represented by $R^5$ is preferably a cycloalkylcarbonyl group having 4 to 9 total carbon atoms. Examples thereof include a cyclopropanecarbonyl group, a cyclobutanecarbonyl group, a cyclopentanecarbonyl group, and a cyclohexanecarbonyl group. Also, examples of the 1,2-cycloalkanediamine having 5 to 8 carbon atoms include a 1,2-cyclopentanediamine, a 1,2-cyclohexanediamine, and a 1, 2-cycloheptanediamine.

The straight- or branched-chain alkyl group represented by $R^6$ is preferably a straight- or branched-chain alkyl group having 1 to 6 carbon atoms. Examples thereof include a methyl group, an ethyl group, an n-propyl group, an isopropyl group, an n-butyl group, a tert-butyl group, an n-pentyl group, and an n-hexyl group. The alkyl group having a halogen atom includes straight- or branched-chain alkyl groups having 1 to 6 carbon atoms which is substituted with 1 to 3 halogen atoms (e.g., fluorine, chlorine, bromine), such as a trifluoromethyl group, a chloroethyl group, and a chloropropyl group. The cycloalkyl group includes cycloalkyl groups having 3 to 8 carbon atoms, such as a cyclopropyl group, a cyclobutyl group, a cyclopentyl group, a cyclohexyl group, and a cycloheptyl group. The aryl group includes aryl groups having 6 to 10 carbon atoms, such as a phenyl group, a tolyl group, a xylyl group, and a naphthyl group. The aralkyl group includes phenyl-$C_{1-4}$-alkyl groups, such as a benzyl group and a phenetyl group.

Examples of the malonic acid residue which may have a substituent group capable of coordinating to the platinum in formula (1) by O,O-coordination include a malonic acid residue, an α-($C_{1-6}$-alkyl) malonic acid residue, an α,α-di ($C_{1-6}$-alkyl) malonic acid residue, and an α-($C_{3-6}$-cycloalkyl) malonic acid residue. Examples of the N-acylamino acid residue include N—$C_{2-8}$-alkanoyl-α-amino acid residues, such as an N-acetylglycine residue, an N-acetylalanine residue, an N-acetylvaline residue, an N-acetylleucine residue, and an N-acetylisoleucine residue. Also, the O,O-coordination means that two carboxyl groups are coordinated to platinum in the case of malonic acid, or a hydroxyl group and a carboxyl group are coordinated to platinum in the case of glycolic acid. The O,N-coordination means that an amino group and a carboxyl group of an amino acid are coordinated to platinum.

The diamine-platinum (IV) complex represented by formula (1) of the present invention also includes solvates such as hydrates. In addition, the compounds of the present invention can exist in various stereochemical forms, and all of these stereochemical forms are included in the present invention.

The diamine-platinum (IV) complex of the present invention can be produced, for example, in accordance with the following methods A to E. Method A:

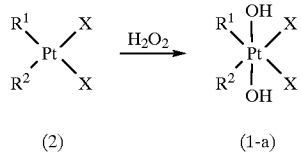

(In the formulae, $R^1$, $R^2$ and X have the same meanings as defined above.)

That is, the compound (1-a) of the present invention is obtained by adding 1 to 10 equivalents, preferably 2 to 5 equivalents, of a 30% hydrogen peroxide aqueous solution to an aqueous solution of a platinum (II) complex (2) and carrying out the reaction at 20 to 80° C., preferably 40 to 60° C., for 1 to 5 hours. The platinum (II) complex (2) used as the starting material can be synthesized in accordance with the method described in JP-A-1-156989 or JP-A-2-256690 or other known methods. Method B

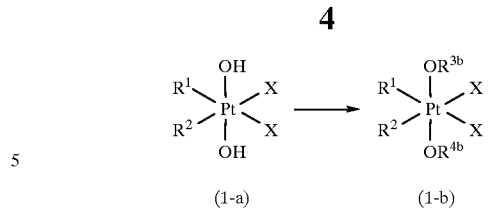

(In the formulae, $R^{3b}$ and $R^{4b}$ each represents groups represented by $R^3$ and $R^4$ excluding a hydrogen atom, and $R^1$, $R^2$ and X have the same meanings as defined above.) That is, the compound (1-b) of the present invention is obtained by allowing the compound (1-a) to react with 2 to 10 equivalents, preferably 3 to 5 equivalents, of an activated carboxylic acid without a solvent or in an anhydrous solvent at 0 to 60° C., preferably 20 to 40° C., for 2 to 8 hours. Examples of the anhydrous solvent include toluene, pyridine, dimethylformamide, and tetrahydrofuran. Examples of the activated carboxylic acid include an acid anhydride and an acid halide.

Method C

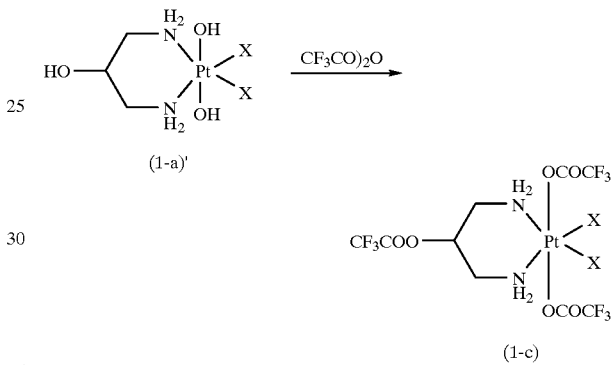

(In the formulae, X has the same meaning as defined above.)

That is, a compound (1-a)' which is a member of the compounds (1-a) synthesized by the method A and has 1,3-diamino-2-propanol as its amine is allowed to react with a trifluoroacetic anhydride at 20 to 40° C. for 1 to 3 days, thereby obtaining the compound (1-c) of the present invention.

Method D

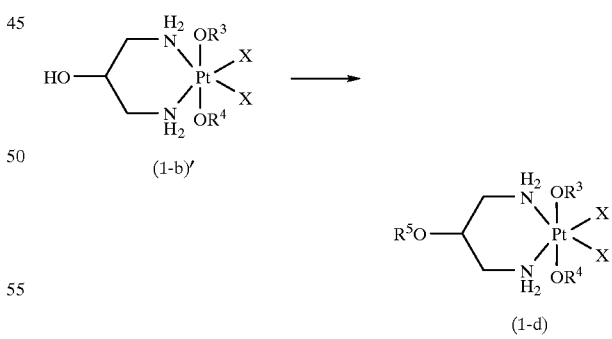

(In the formulae, $R^3$, $R^4$, $R^5$ and X have the same meanings as defined above.)

That is, a compound (1-b)' which is a member of the compounds (1-b) synthesized by the method B and has 1,3-diamino-2-propanol as its amine is allowed to react with 2 to 10 equivalents, preferably 3 to 5 equivalents, of an activated carboxylic acid or an activated sulfonic acid at 0 to 60° C., preferably 20 to 40° C., for 2 to 8 hours in an anhydrous solvent, thereby obtaining the compound (1-d) of the present invention. Examples of the anhydrous solvent include toluene, pyridine, dimethylformamide, and tetrahydrofuran. Examples of the activated carboxylic acid and sulfonic acid include an acid anhydride and an acid halide.

Method E

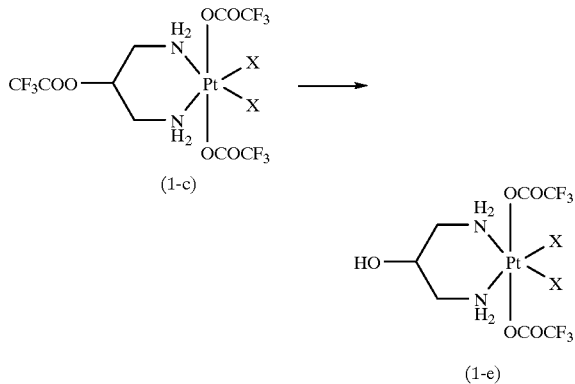

(In the formulae, X has the same meaning as defined above.)

That is, the compound (1-e) of the present invention is obtained by allowing the compound (1-c) synthesized by the method C to react in a lower alcohol, preferably methanol, at 20 to 50° C. for 4 to 24 hours.

The compounds of the present invention synthesized by the above methods can be purified into more pure forms by the usual way.

As will be described later in Examples, the platinum complex of the present invention has excellent antitumor effects and high safety. When the platinum complex of the present invention is used as a pharmaceutical composition such as an antitumor agent or the like, its suitable dose is 1 to 50 mg per 1 kg body weight per day in the case of oral administration or 0.5 to 18 mg per 1 kg body weight per day in the case of parenteral administration, though it varies depending on the body weight, age, sex, administration method, physical condition, morbid state and the like of each patient.

The pharmaceutical composition of the present invention can be made into various dosage forms, such as tablets, granules, powders, capsules, suspensions, injections, and suppositories, in the usual way. When a solid pharmaceutical composition is produced for use in oral administration, the compound of the present invention is mixed with a filler, as well as a binder, a disintegrator, a lubricant, a coloring agent, a corrective, an extender, a coating material, a sugar-coating material and the like as occasion demands, and then made into dosage forms, such as tablets, granules, powders, and capsules. When injections are prepared, the compound of the present invention is dissolved in a solvent, such as distilled water for injection use, a physiological saline, a 5% glucose aqueous solution, an ethanol aqueous solution, a glycerol aqueous solution, and a propylene glycol aqueous solution, as occasion demands and then made into injections for subcutaneous, intravenous or intramuscular injection use in the usual way. When suppositories are produced, the compound of the present invention is added to a cacao butter or medium chain fatty acid glycerol ester base and mixed under heating, and the mixture is made into suppositories in the usual way. Of these administration modes, injections or oral preparations are preferred and oral preparations are particularly preferred.

The diamine-platinum (IV) complex of the present invention has excellent antitumor action, has high safety and is effective for oral administration, so that it is useful as an antitumor agent.

The present invention is described further in detail with reference to the following examples which, however, do not restrict the invention in any way.

EXAMPLE 1 (Compound 1)

A 3.15 g (7.4 mmol) portion of 1,1-cyclobutanedicarboxylato (1,3-diamino-2-propanol) platinum (II) was dissolved in 50 ml of water under heating at 50° C., and then 2 ml of a 30% hydrogen peroxide aqueous solution was added thereto to carry out the reaction for 2 hours. After completion of the reaction, the reaction solution was concentrated and the thus precipitated white crystals were collected by filtration, washed with a small amount of cold water and then dried under a reduced pressure to obtain 2.80 g (yield: 82.5%) of 1,1-cyclobutanedicarboxylato trans-dihydroxo (1,3-diamino-2-propanol)platinum (IV) in the form of white crystals.

Melting point: 210–215° C. (decomp.)

$^1$H-NMR ($D_2O$): 4.45 (1H, t), 2.9–3.0 (2H, m), 2.66 (4H, t), 2.3–2.5 (2H, m), 2.03 (2H, quint.)

EXAMPLE 2 (Compound 2)

The procedure of Example 1 was repeated except that 2.40 g (6.7 mmol) of (glycolato-O,O') (1,3-diamino-2-propanol)platinum (II) was used instead of 1,1-cyclobutanedicarboxylato (1,3-diamino-2-propanol) platinum (II), thereby obtaining 2.10 g (yield: 79.8%) of trans-dihydroxo(glycolato-O,O') (1,3-diamino-2-propanol) platinum (IV) in the form of white crystals.

Melting point: 185–200° C. (decomp.) $^1$H-NMR ($D_2O$): 4.41 (1H, t), 4.25–4.35 (2H, m), 2.9–3.0 (2H, m), 2.6–2.8 (1H, m), 2.35–2.55 (1H, m)

EXAMPLE 3 (Compound 3)

The procedure of Example 1 was repeated except that 2.48 g (6.2 mmol) of (N-acetylglycinato-N,O) (1,3-diamino-2-propanol)platinum (II) was used instead of 1,1-cyclobutanedicarboxylato (1,3-diamino-2-propanol) platinum (II), thereby obtaining 2.58 g (yield: 95.9%) of (N-acetylglycinato-N,O) trans-dihydroxo-(1,3-diamino-2-propanol)platinum (IV) in the form of white crystals.

Melting point: 210–215° C. (decomp.)

$^1$H-NMR ($D_2O$): 4.40 (1H, t), 4.37 (2H, AB q), 3.0–3.1 (1H, m), 2.9–3.0 (1H, m), 2.6–2.8 (1H, m), 2.2–2.4 (1H, m), 2.13 (3H, s)

EXAMPLE 4 (Compound 4)

The procedure of Example 1 was repeated except that 2.12 g (5 mmol) of (N-acetylglycinato-N,O) (trans(1R,2R)-1,2-cyclohexanediamine)platinum (II) was used instead of 1,1-cyclobutanedicarboxylato (1,3-diamino-2-propanol) platinum (II), thereby obtaining 1.85 g (yield: 80.8%) of (N-acetylglycinato-N,O) trans-dihydroxo(trans(1R,2R)-1,2-cyclohexanediamine)platinum (IV) in the form of white crystals.

Melting point: 210–215° C. (decomp.)

$^1$H-NMR ($D_2O$): 4.34 (2H, AB q), 2.7–2.9 (2H, m), 2.25–2.35 (2H, m), 2.15 (3H, s), 1.45–1.70 (4H, m), 1.2–1.3 (2H, m)

EXAMPLE 5 (Compound 5)

A 1.4 g (3 mmol) portion of 1,1-cyclobutanedicarboxylato trans-dihydroxo(1,3-diamino-2-propanol)platinum (IV) (compound 1) was suspended in 15 ml of acetic anhydride, and the reaction was carried out at room temperature for 5 hours and then at 40° C. for 3 hours. After cooling, the reaction solution was diluted with ether, and the thus precipitated white powder was collected by filtration, thereby obtaining 1.36 g (yield: 83.3%) of trans-bis (acetato) 1,1-cyclobutanedicarboxylato (1,3-diamino-2-propanol) platinum (IV) in the form of white powder.

Melting point: 200–205° C. (decomp.)

$^1$H-NMR (D$_2$O): 4.43 (1H, t), 2.8–2.9 (2H, m), 2.61 (2H, t), 2.53 (2H, t), 2.3–2.4 (2H, m), 2.05 (3H, s), 2.03 (3H, s), 1.97 (2H, quint.)

EXAMPLE 6 (Compound 6)

The procedure of Example 5 was repeated except that 1.00 g (2.5 mmol) of (N-acetylglycinato-N,O) trans-dihydroxo(1,3-diamino-2-propanol)platinum (IV) (compound 3) was used instead of 1,1-cyclobutanedicarboxylato trans-dihydroxo(1,3-diamino-2-propanol)platinum (IV), thereby obtaining 0.65 g (yield: 54.3%) of (N-acetylglycinato-N,O) trans-bis(acetato) (1,3-diamino-2-propanol)platinum (IV) in the form of white powder.

Melting point: 195–200° C. (decomp.)

$^1$H-NMR (D$_2$O): 4.38 (1H, t), 4.26 (2H, AB q), 2.9–3.0 (1H, m), 2.75–2.85 (1H, m), 2.6–2.7 (1H, m), 2.1–2.3 (1H, m), 2.09 (6H, s), 2.08 (3H, s)

EXAMPLE 7 (Compound 7)

The procedure of Example 5 was repeated except that 1.80 g (3.9 mmol) of (N-acetylglycinato-N,O) trans-dihydroxo(trans(1R,2R)-1,2-cyclohexanediamine)platinum (IV) (compound 4) was used instead of 1,1-cyclobutanedicarboxylato trans-dihydroxo(1,3-diamino-2-propanol)platinum (IV), thereby obtaining 1.27 g (yield: 60.1%) of trans-bis(acetato) (N-acetylglycinato-N,O) (trans (1R,2R)-1,2-cyclohexanediamine)platinum (IV) in the form of yellowish white powder.

Melting point: 180–185° C. (decomp.)

$^1$H-NMR (D$_2$O): 4.28 (2H, m), 2.70–2.85 (2H, m), 2.20–2.35 (2H, m), 2.12 (3H, s), 2.07 (6H, s), 1.4–1.7 (4H, m), 1.2–1.3 (2H, m)

EXAMPLE 8 (Compound 8)

A 1.83 g (4 mmol) portion of (N-acetylglycinato-N,O) trans-dihydroxo(trans(1R,2R)-1,2-cyclohexanediamine) platinum (IV) was suspended in 10 ml of toluene, and then 0.4 ml of pyridine was added thereto. At room temperature, 4.1 g (18 mmol) of benzoic anhydride was added thereto to carry out the reaction overnight. The reaction solution was concentrated and mixed with ether, and the thus precipitated powder was collected by filtration. By purifying the thus collected powder by silica gel column chromatography, 0.62 g (yield: 23.3%) of (N-acetylglycinato-N,O) trans-benzoato hydroxo(trans(1R,2R)-1,2-cyclohexanediamine)platinum (IV) was obtained in the form of yellowish white powder.

Melting point: 200–205° C. (decomp.)

$^1$H-NMR (methanol-d$_4$): 7.94 (2H, m), 7.47 (1H, m), 7.38 (2H, m), 4.75 (2H, AB q), 2.8–2.9 (1H, m), 2.7–2.8 (1H, m), 2.2–2.4 (2H, m), 2.10 (3H, s), 1.5–1.8 (4H, m), 1.2–1.4 (2H, m)

EXAMPLE 9 (Compound 9)

A 1.83 g (4 mmol) portion of (N-acetylglycinato-N,O) trans-dihydroxo(trans(1R,2R)-1,2-cyclohexanediamine) platinum (IV) was suspended in 30 ml of toluene, and then 1 ml of pyridine was added thereto. At room temperature, the reaction was carried out for 4 hours by adding 1.4 g (10 mmol) of benzoyl chloride. The reaction solution was concentrated, and the resulting residue was purified by silica gel column chromatography, thereby obtaining 0.9 g (yield: 33.8%) of (N-acetylglycinato-N,O) trans-bis(benzoato) (trans(1R,2R)-1,2-cyclohexanediamine)platinum (IV) in the form of yellow powder.

Melting point: 200–205° C. (decomp.)

$^1$H-NMR (chloroform-d): 9.5 (1H, br.), 8.7 (1H, br.), 8.2 (1H, br.), 7.8 (1H, br.), 8.00 (5H, m), 7.1–7.6 (5H, m), 4.13 (2H, s), 2.7–3.0 (2H, m), 2.2–2.5 (2H, m), 2.22 (3H, s), 1.5–1.7 (3H, m), 1.45 (1H, m), 1.1–1.3 (2H, m)

EXAMPLE 10 (Compound 10)

The procedure of Example 9 was repeated except that n-butyryl chloride was used instead of benzoyl chloride, thereby obtaining 1.38 g (yield: 57.7%) of (N-acetylglycinato-N,O) trans-bis (butyrato) (trans-(1R, 2R)-1,2-cyclohexanediamine)platinum (IV) in the form of yellow powder.

Melting point: 125–130° C. (decomp.)

$^1$H-NMR (chloroform-d): 9.6 (1H, br.), 8.3 (1H, br.), 7.9 (1H, br.), 7.6 (1H, br.), 4.12 (2H, AB q), 2.7–2.9 (1H, m), 2.5–2.7 (1H, m), 2.2–2.4 (6H, m), 2.15 (3H, s), 1.5–1.7 (6H, m), 1.15–1.45 (4H, m), 0.89 (3H, t), 0.87 (3H, t)

EXAMPLE 11 (Compound 11)

A 1.39 g (3 mmol) portion of 1,1-cyclobutanedicarboxylato trans-dihydroxo(1,3-diamino-2-propanol)platinum (IV) was suspended in 20 ml of trifluoroacetic anhydride to carry out the reaction at room temperature for 3 days. The thus precipitated white powder was collected by filtration to obtain 1.5 g (yield: 66.8%) of 1,1-cyclobutanedicarboxylato trans-bis(trifluoroacetato) (O-trifluoroacetyl-1,3-diamino-2-propanol)platinum (IV) in the form of white powder.

Melting point: 195–200° C. (decomp.)

$^1$H-NMR (dimethylformamide-d$_7$): 8.58 (2H, br.), 8.12 (2H, br.), 5.94 (1H, t), 3.2–3.3 (2H, m), 2.9–3.1 (2H, m), 2.7–2.8 (2H, m), 2.37 (2H, t), 1.91 (2H, quint.)

EXAMPLE 12 (Compound 12)

A 1.1 g (2 mmol) portion of trans-bis(acetato) 1,1-cyclobutanedicarboxylato (1,3-diamino-2-propanol) platinum (IV) (compound 5) was suspended in 4 ml of dimethylformamide, and then 4 ml of pyridine was added thereto. Next, the reaction solution was mixed with 0.35 ml of acetic anhydride at room temperature to carry out the reaction for 4 hours. The reaction solution was diluted with acetone, and the thus precipitated white powder was collected by filtration, thereby obtaining 0.6 g (yield: 51.1%) of trans-bis(acetato) 1,1-cyclobutanedicarboxylato (O-acetyl-1,3-diamino-2-propanol)platinum (IV) in the form of white powder.

Melting point: 240–245° C. (decomp.)

$^1$H-NMR (D$_2$O): 5.50 (1H, t), 3.03 (2H, d), 2.65 (2H, t), 2.4–2.7 (4H, m), 2.15 (3H, s), 2.11 (3H, s), 2.06 (3H, s), 1.99 (2H, quint.)

EXAMPLE 13 (Compound 13)

A 1.14 g (2.63 mmol) portion of (N-acetylglycinato-N,O) trans-dihydroxo(1,3-diamino-2-propanol)platinum (IV) was suspended in 20 ml of pyridine, and the suspension was mixed with 1.5 ml of acetic anhydride to carry out the reaction at 50° C. for 2 hours. The reaction solution was concentrated, and the resulting residue was purified by silica gel column chromatography, thereby obtaining 1.02 g (yield: 69.3%) of (N-acetylglycinato-N,O) trans-bis(acetato) (O-acetyl-1,3-diamino-2-propanol)platinum (IV) in the form of yellowish white powder.

Melting point: 195–200° C. (decomp.)

$^1$H-NMR (chloroform-d +methanol-$d_4$): 11.5 (1H, br.), 8.5 (1H, br.), 6.8 (1H, br.), 6.5 (1H, br.), 5.31 (1H, m), 4.16 (2H, AB q), 2.8–3.0 (3H, m), 2.2–2.3 (1H, m), 2.17 (3H, s), 2.09 (3H, s), 2.07 (3H, s), 2.06 (3H, s)

EXAMPLE 14 (Compound 14)

A 1.1 g (2 mmol) portion of trans-bis(acetato) 1,1-cyclobutanedicarboxylato (1,3-diamino-2-propanol) platinum (IV) was suspended in 30 ml of pyridine, and then 0.1 g of 4,4-dimethylaminopyridine was added thereto. Next, the reaction solution was mixed with 0.678 g (3 mmol) of benzoic anhydride to carry out the reaction at 50° C. for 1 hour. The reaction solution was concentrated and mixed with acetone, and the thus precipitated white powder was collected by filtration, thereby obtaining 1.25 g (yield: 96.3%) of trans-bis(acetato) 1,1-cyclobutanedicarboxylato (O-benzoyl-1,3-diamino-2-propanol)platinum (IV) in the form of white powder.

Melting point: 195–200° C. (decomp.)

$^1$H-NMR (dimethylformamide-$d_7$+$D_2O$): 8.1–8.2 (2H, m), 7.6–7.7 (1H, m), 7.5–7.6 (2H, m), 5.65 (1H, m), 3.15–3.25 (2H, m), 2.75–2.85 (1H, m), 2.64 (2H, t), 2.47 (2H, t), 1.92 (3H, s), 1.89 (3H, s), 1.8–2.0 (3H, m)

EXAMPLE 15 (Compound 15)

The procedure of Example 14 was repeated except that 1.04 g (2 mmol) of (N-acetylglycinato-N,O) trans-bis (acetato) (1,3-diamino-2-propanol)platinum (IV) was used instead of trans-bis(acetato) 1,1-cyclobutanedicarboxylato (1,3-diamino-2-propanol)platinum (IV), thereby obtaining 0.5 g (yield: 40.2%) of (N-acetylglycinato-N,O) trans-bis (acetato) (O-benzoyl-1,3-diamino-2-propanol)platinum (IV) in the form of yellowish white powder.

Melting point: 160–165° C. (decomp.)

$^1$H-NMR (chloroform-d): 11.5 (1H, br. t), 8.1–8.2 (2H, m), 7.60 (2H, m), 7.46 (2H, m), 6.8 (1H, br. t), 6.4 (1H, br. t), 5.62 (1H, m), 4.11 (2H, AB q), 3.0–3.5 (3H, m), 2.3–2.5 (1H, m), 2.08 (3H, s), 2.07 (3H, s), 2.04 (3H, s)

EXAMPLE 16 (Compound 16)

A 1.04 g (2 mmol) portion of (N-acetylglycinato-N,O) trans-bis(acetato) (1,3-diamino-2-propanol)platinum (IV) was suspended in 10 ml of dimethylformamide, and then 10 ml of pyridine was added thereto. At room temperature, the reaction solution was mixed with 0.5 g of cyclopropanecarboxylic acid chloride to carry out the reaction for 7 hours. The reaction solution was concentrated, and the resulting residue was purified by silica gel column chromatography and alumina column chromatography and then made into powder with isopropyl ether, thereby obtaining 0.42 g (yield: 35.8%) of (N-acetylglycinato-N,O) trans-bis(acetato) (O-cyclopropanecarbonyl-1,3-diamino-2-propanol) platinum (IV) in the form of yellow powder.

Melting point: 145–150° C. (decomp.)

$^1$H-NMR (chloroform-d): 11.4 (1H, br. t), 8.4 (1H, br. t), 6.8 (1H, br. t), 6.2 (1H, br. t), 5.35 (1H, m), 4.14 (2H, m), 2.8–3.2 (3H, m), 2.1–2.3 (1H, m), 2.09 (3H, s), 2.06 (6H, s), 1.69 (1H, m), 1.26 (2H, m), 0.96 (2H, m)

EXAMPLE 17 (Compound 17)

A 1.04 g (2 mmol) portion of (N-acetylglycinato-N,O) trans-bis(acetato) (1,3-diamino-2-propanol)platinum (IV) was suspended in 30 ml of pyridine, and then 0.45 g of methanesulfonic anhydride which had been dissolved in 10 ml of anhydrous tetrahydrofuran was added dropwise thereto at room temperature. Three hours later, the reaction solution was concentrated, and the resulting residue was purified by silica gel column chromatography, thereby obtaining 0.15 g (yield: 12.6%) of (N-acetylglycinato-N,O) trans-bis(acetato) (O-methanesulfonyl- 1,3-diamino-2-propanol)platinum (IV) in the form of yellowish white powder.

Melting point: 190–195° C. (decomp.)

$^1$H-NMR ($D_2O$): 5.48 (1H, t), 4.28 (2H, AB q), 3.34 (3H, s), 3.25 (1H, d), 3.15 (1H, d), 3.01 (1H, dd), 2.54 (1H, dd), 2.11 (6H, s), 2.10 (3H, s)

EXAMPLE 18 (Compound 18)

A 3.26 g (5 mmol) portion of 1,1-cyclobutanedicarboxylato trans-bis(trifluoroacetato) (O-trifluoroacetyl-1,3-diamino-2-propanol)platinum (IV) (compound 11) was suspended in 200 ml of methanol to carry out the reaction at 40° C. for 6 hours. After cooling, the reaction solution was concentrated, the resulting residue was mixed with acetone and then the thus precipitated white powder was collected by filtration, thereby obtaining 2.18 g (yield: 66.8%) of 1,1-cyclobutanedicarboxylato trans-bis (trifluoroacetato) (1,3-diamino-2-propanol)platinum (IV) in the form of white powder.

Melting point: 195–200° C. (decomp.)

$^1$H-NMR (methanol-$d_4$): 4.36 (1H, t), 2.7–2.8 (4H, m), 2.44 (2H, t), 2.2–2.4 (2H, m), 1.98 (2H, quint.)

Test Example 1

Test on antitumor effect on mouse M5076 tumor

A total of $1 \times 10^6$ cells of mouse M5076 tumor were transplanted subcutaneously (s.c.) of a 6-week age male $BDF_1$ mouse, a drug (compound of the present invention) was administered orally (p.o.) once a day for 5 days starting on the next day and then, after 30 days of observation, growth inhibition rate (GI) was calculated from the average tumor weights in the drug-treated group and the non-treated group. Also, an $ID_{50}$ value (a dosage by which the GI value after 5 administrations shows 50%) was calculated from a linear regression line based on the GI value of each sample with each dosage, and a therapeutic index (TI) was calculated from an $LD_{50}$ value (50% lethal dose by single intraperitoneal administration) obtained at the time of the dose setting. Each of the drugs to be tested was prepared just before its use by dissolving or suspending the drug (compound of the present invention) in olive oil using a handy sonicator. The dosage was 0.1 ml per 10 g mouse body weight. The results are shown in Table 1. In Table 1, $GI_{max}$ is the maximum value (%) of GI in the dosage range by which no mortal case can be found, and its dosage (mg/kg) is shown in parentheses.

TABLE 1

Antitumor effect on M5076 reticulosarcoma (s.c.-p.o.)

| Test drug | $GI_{max}$ | $LD_{50}$ (mg/kg) | $ID_{50}$ (mg/kg) | TI |
|---|---|---|---|---|
| Cisplatin | 74.5 | (8.0) | 18.0 | 3.2 | 5.6 |
| Carboplatin | 75.3 | (256.0) | 245.0 | 119.9 | 2.0 |
| Compound 1 | 95.6 | (32.0) | >200.0 | <8.0 | >25.0 |
| Compound 5 | 61.4 | (64.0) | 353.0 | 38.4 | 9.2 |
| Compound 11 | 86.5 | (32.0) | 176.5 | 10.2 | 17.3 |
| Compound 18 | 95.6 | (32.0) | 176.8 | 9.6 | 18.4 |

While the invention has been described in detail and with reference to specific embodiments thereof, it will be apparent to one skilled in the art that various changes and modifications can be made therein without departing from the spirit and scope thereof.

This application is based on Japanese application No. Hei 9-60645 filed on Mar. 14, 1997, the entire content of which is incorporated hereinto by reference.

What is claimed is:

1. A diamine-platinum (IV) complex represented by the following formula (1):

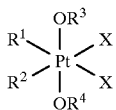

wherein $R^1$ and $R^2$ together represent the following group (A):

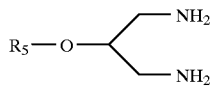

in which $R^5$ represents a hydrogen atom, an acetyl group, a trifluoroacetyl group, a benzoyl group, a cycloalkylcarbonyl group or a methanesulfonyl group $R^3$ and $R^4$ are the same or different and each represents a hydrogen atom or a group $R^6CO$— in which $R^6$ represents a straight- or branched-chain alkyl group, an alkyl group having a halogen atom, a cycloalkyl group, an aryl group or an aralkyl group; and two X's together represent a malonic acid residue or glycolic acid residue which may have a substituent capable of coordinating to the platinum in formula (1) by an O,O-coordination or an N-acylamino acid residue coordinating to the platinum in formula (1) by an O,N-coordination, or a salt thereof.

2. The diamine-platinum (IV) complex according to claim 1, wherein the cycloalkylcarbonyl group represented by $R^5$ is a cycloalkylcarbonyl group having 4 to 9 total carbon atoms.

3. The diamine-platinum (IV) complex according to claim 1, wherein the cycloalkylcarbonyl group represented by $R^5$ is elected from the group consisting of a cyclopropanecarbonyl group, a cyclobutanecarbonyl group, a cyclopentanecarbonyl group, and a cyclohexanecarbonyl group.

4. The diamine-platinum (IV) complex according to claim 1, wherein the 1,2-cycloalkanediamine having 5 to 8 carbon atoms represented by $R^5$ is selected from the group consisting of a 1,2-cyclopentanediamine, a 1,2-cyclohexanediamine, and a 1,2-cycloheptanediamine.

5. The diamine-platinum (IV) complex according to claim 1, wherein the straight- or branched-chain alkyl group represented by $R^6$ is a straight- or branched-chain alkyl group having 1 to 6 carbon atoms.

6. The diamine-platinum (IV) complex according to claim 1, wherein the straight- or branched-chain alkyl group represented by $R^6$ is selected from the group consisting of a methyl group, an ethyl group, an n-propyl group, an iso-propyl group, an n-butyl group, a tert-butyl group, an n-pentyl group, and an n-hexyl group.

7. The diamine-platinum (IV) complex according to claim 1, wherein the alkyl group having a halogen atom represented by $R^6$ is a straight- or branched-chain alkyl group 1 to 6 carbon atoms which is substituted with 1 to 3 halogen atoms.

8. The diamine-platinum (IV) complex according to claim 1, wherein the alkyl group having a halogen atom represented by $R^6$ is selected from the group consisting of a trifluoromethyl group, a chloroethyl group, and a chloropropyl group.

9. The diamine-platinum (IV) complex according to claim 1, wherein the cycloalkyl group represented by $R^6$ is a cycloalkyl group having 3 to 8 carbon atoms.

10. The diamine-platinum (IV) complex according to claim 1, wherein the cycloalkyl group represented by $R^6$ is selected from the group consisting of a cyclopropyl group, a cyclobutyl group, a cyclopentyl group, a cyclohexyl group, and a cycloheptyl group.

11. The diamine-platinum (IV) complex according to claim 1, wherein aryl group represented by $R^6$ is an aryl group having 6 to 10 carbon atoms.

12. The diamine-platinum (IV) complex according to claim 1, wherein the aryl group represented by $R^6$ is selected from the consisting of a phenyl group, a tolyl group a xylyl group, and a naphthyl group.

13. The diamine-platinum (IV) complex according to claim 1, wherein the aralkyl group represented by $R^6$ is a phenyl-$C_{1-4}$-alkyl group.

14. The diamine-platinum (IV) complex according to claim 1, wherein the aralkyl group represented by $R^6$ is selected from the group consisting of a benzyl group and a phenetyl group.

15. The diamine-platinum (IV) complex according to claim 1, wherein the malonic acid residue is selected from the group consisting of a malonic acid residue, an α-($C_{1-6}$-alkyl) malonic acid residue, an α,α-di($C_{1-6}$-alkyl) malonic acid residue, and an α-($C_{3-6}$-cycloalkyl) malonic acid residue.

16. The diamine-platinum (IV) complex according to claim 1, wherein the N-acylamino acid residue is an N-$C_{2-8}$-alkanoyl-α-amino acid residue.

17. The diamine-platinum (IV) complex according to claim 1, wherein the N-acylamino acid residue is selected from the group consisting of an N-acetylglycine residue, an N-acetylalanine residue, an N-acetylvaline residue, an N-acetylleucine residue, and an N-acetylisoleucine residue.

18. A pharmaceutical composition comprising as an active ingredient the diamine-platinum (IV) complex according to claim 1 or a pharmaceutically acceptable salt thereof, optionally together with a pharmaceutically acceptable carrier or diluent.

19. A method for preventing or treating a tumor comprising as an active ingredient administering to human or animal in need of such prevention or treatment an effective amount of the diamine-platinum (IV) complex according to claim 1 or a pharmaceutically acceptable salt thereof, optionally together with a pharmaceutically acceptable carrier or diluent.

20. A diamine-platinum (IV) complex represented by the following formula (1):

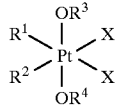
(1)

wherein $R^1$ and $R^2$ together represent the following group (A):

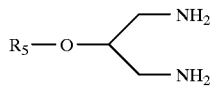
(A)

in which $R^5$ represents a hydrogen atom, an acetyl group, a trifluoroacetyl group, a benzoyl group, a cycloalkylcarbonyl group or a methanesulfonyl group, or a 1,2-cylcloalkanediamine having 5 to 8 carbon atoms which can represent all stereochemical structures, cis (R,S), trans (1S, 2S), and trans (1R,2R);

$R^3$ and $R^4$ are the same or different and each represents a group $R^6CO-$ in which $R^6$ represents an alkyl group having a halogen atom, a cycloalkyl group, an aryl group or an aralkyl group; and two X's together represent a malonic acid residue or glycolic acid residue which may have a substituent capable of coordinating to the platinum in formula (1) by an O,O-coordination or an N-acylamino acid residue coordinating to the platinum in formula (1) by an O,N-coordination, or a salt thereof.

21. A diamine-platinum (IV) complex represented by the following formula (1):

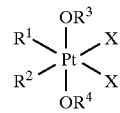
(1)

wherein $R^1$ and $R^2$ together represent the following group (A):

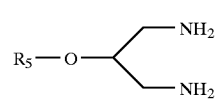
(A)

in which $R^5$ represents a hydrogen atom, an acetyl group, a trifluoroacetyl group, a benzoyl group, a cycloalkylcarbonyl group or a methanesulfonyl group, or a 1,2-cylcloalkanediamine having 5 to 8 carbon atoms which can represent all stereochemical structures, cis (R,S), trans (1S, 2S), and trans (1R,2R);

$R^3$ and $R^4$ are the same or different and each represents a hydrogen atom or a group $R^6CO-$ in which $R^6$ represents a straight- or branched-chain alkyl group, an alkyl group having a halogen atom, a cycloalkyl group, an aryl group or an aralkyl group; and two X's together represent an N-acylamino acid residue coordinating to the platinum in formula (1) by an O,N-coordination, or a salt thereof.

* * * * *